US007918836B2

(12) United States Patent
Gill et al.

(10) Patent No.: US 7,918,836 B2
(45) Date of Patent: Apr. 5, 2011

(54) OSTOMY BAG WITH IRRIGATION SYSTEM

(76) Inventors: Zora Singh Gill, Bakersfield, CA (US);
Nichhater Singh Gill, Bakersfield, CA (US)

(*) Notice: Subject to any disclaimer, the term of this patent is extended or adjusted under 35 U.S.C. 154(b) by 124 days.

(21) Appl. No.: 12/387,360

(22) Filed: May 1, 2009

(65) Prior Publication Data
US 2010/0016819 A1    Jan. 21, 2010

Related U.S. Application Data

(60) Provisional application No. 61/135,101, filed on Jul. 15, 2008.

(51) Int. Cl.
*A61F 5/44* (2006.01)
(52) U.S. Cl. ........ 604/333; 604/334; 604/335; 604/337; 604/339; 604/340; 604/341; 604/332
(58) Field of Classification Search ............... 604/332, 604/333, 334, 337, 339, 340, 341
See application file for complete search history.

(56) References Cited

U.S. PATENT DOCUMENTS

| | | | |
|---|---|---|---|
| 1,687,012 A * | 10/1928 | Forth | 134/44 |
| 2,310,505 A | 2/1943 | Blackbum et al. | |
| 2,648,335 A | 8/1953 | Chambers | |
| 2,887,109 A * | 5/1959 | Barrington | 604/92 |
| 3,282,412 A | 11/1966 | Corella et al. | |
| 3,292,626 A | 12/1966 | Schneider | |
| 3,295,145 A | 1/1967 | Erickson | |
| 3,297,152 A | 1/1967 | Corella et al. | |
| 3,405,714 A | 10/1968 | Moss | |
| 3,559,651 A | 2/1971 | Moss | |
| 3,618,606 A | 11/1971 | Brown et al. | |
| 3,780,739 A | 12/1973 | Frank | |
| 3,822,704 A | 7/1974 | Nolan | |
| 3,902,496 A * | 9/1975 | Eakin | 604/334 |
| 4,084,590 A | 4/1978 | Caraway et al. | |

(Continued)

FOREIGN PATENT DOCUMENTS
WO     WO 94/27530      12/1994
(Continued)

OTHER PUBLICATIONS http://www.kemonline.com/products.htm; KEM Enterprises, Inc.
(Continued)

*Primary Examiner* — Tatyana Zalukaeva
*Assistant Examiner* — Ginger T Chapman
(74) *Attorney, Agent, or Firm* — James M. Duncan, Esq.;
Klein, DeNatale, Goldner, Cooper, et al.

(57) ABSTRACT

The ostomy bag comprises an outer chamber comprising an upper portion and a lower portion, and an inner chamber. The inner chamber may comprise a one-way valve that limits the back flow of the bodily wastes from the lower portion of the bag to the upper portion. The one-way valve may comprise a biasing member and the biasing member may have a length that is longer then the length of the bottom of the inner chamber walls. The bag may comprise an irrigation system that provides for the flushing of both the inner and the outer chambers simultaneously. The irrigation tube of the irrigation system may comprise slits along the portion of the irrigation tube that resides within the inner chamber and the lower portion of the outer chamber.

15 Claims, 4 Drawing Sheets

U.S. PATENT DOCUMENTS

| | | | | |
|---|---|---|---|---|
| 4,180,072 A | * | 12/1979 | Sneider | 604/32 |
| 4,194,506 A | * | 3/1980 | Voorhies | 604/334 |
| 4,285,076 A | * | 8/1981 | Dickstein | 4/341 |
| 4,300,560 A | | 11/1981 | Steer et al. | |
| 4,319,569 A | * | 3/1982 | Hu | 604/32 |
| 4,533,354 A | | 8/1985 | Jensen | |
| 4,604,095 A | | 8/1986 | Samuelsen | |
| 4,654,037 A | * | 3/1987 | Fenton | 604/334 |
| 4,723,944 A | | 2/1988 | Jensen | |
| 5,074,851 A | | 12/1991 | Plass et al. | |
| 5,096,503 A | * | 3/1992 | Wellman | 134/22.18 |
| 5,364,378 A | | 11/1994 | Denard | |
| 5,573,187 A | * | 11/1996 | Proctor | 239/532 |
| 5,738,668 A | | 4/1998 | Bugajski | |
| 6,050,983 A | | 4/2000 | Moore et al. | |
| 6,106,508 A | | 8/2000 | Lavender | |
| 6,165,159 A | * | 12/2000 | Blanton | 604/333 |
| 6,171,288 B1 | * | 1/2001 | Wiltshire | 604/333 |
| 6,224,581 B1 | * | 5/2001 | Withers et al. | 604/334 |
| 6,328,719 B1 | | 12/2001 | Holtermann et al. | |
| 6,527,755 B1 | | 3/2003 | Salama | |
| 6,695,825 B2 | * | 2/2004 | Castles | 604/332 |
| 6,918,898 B2 | | 7/2005 | King | |
| 7,513,894 B2 | * | 4/2009 | Howlett | 604/355 |
| 2003/0073974 A1 | * | 4/2003 | Falconer | 604/514 |
| 2005/0283126 A1 | | 12/2005 | Schena et al. | |
| 2006/0079854 A1 | | 4/2006 | Kay et al. | |
| 2006/0111682 A1 | | 5/2006 | Schena et al. | |
| 2006/0155252 A1 | * | 7/2006 | Walker et al. | 604/334 |
| 2006/0253090 A1 | | 11/2006 | Bradley et al. | |
| 2008/0228155 A1 | | 9/2008 | Longstaff | |
| 2010/0278456 A1 | * | 11/2010 | Gill et al. | 383/38 |

FOREIGN PATENT DOCUMENTS

| | | |
|---|---|---|
| WO | WO 2006/000985 A2 | 1/2006 |
| WO | WO 2006/000985 A3 | 1/2006 |

OTHER PUBLICATIONS http://www.flat-d.com/ostomyproducts.html; Flat-D Innovations, Inc.

* cited by examiner

OSTOMY BAG WITH IRRIGATION SYSTEM

CROSS-REFERENCE TO RELATED APPLICATIONS

U.S. Provisional Application No. 61/135,101 for this invention was filed on Jul. 15, 2008, for which application these inventors claim domestic priority, and which is incorporated in its entirety.

BACKGROUND OF THE INVENTION

The disclosed device generally relates to devices used for ostomy appliances, and specifically to ostomy appliances having an integral cleaning system, such as colostomy appliances, ileostomy appliances, and urostomy appliances.

In many cases a consequence of surgery for diseases in the gastrointestinal tract is that the colon has been surgically exposed, and the patient is left with an abdominal stoma. The effluents or waste products of the body conveyed through the gastrointestinal tract are discharged through this artificial orifice or opening, and are collected in a collection bag, which is usually adhered to the skin by means of an adhesive wafer or plate having an inlet opening for accommodating the stoma.

Ostomy appliances are well known. Such appliances may be two-piece or one-piece appliances. In both types of appliances, an adhesive barrier member, or base plate, is attached to the wearer. In the case of a one-piece appliance, a receiving member or bag is attached to the base plate. In the case of a two-piece appliance, the adhesive barrier member forms part of a body side member and a receiving member or bag is releasably attached to the body side ostomy member for receiving wastes from the stoma. When using one-piece appliances, the whole appliance, including the adhesive skin barrier securing the appliance to the skin is normally removed and replaced by a fresh place up to several days, and only the receiving member or bag attached to the body side member is replaced. The attachment means for attaching an ostomy receiving bag may be matching coupling rings or matching flanges and adhesive surfaces engaging with and sealing against a flange area of the body side member.

The presently disclosed ostomy bag overcomes several shortcomings of the prior ostomy bags. The disclosed ostomy bag protects the stoma area from significant contact with excreted wastes and any digestive fluids contained within the wastes, and limits the duration of time the wastes are in contact with the stoma. Exposure of the stoma to fluids, and especially to the corrosive attack from stomach acid, causes pain to the wearer. Cleaning of the known bags can be problematic because a complete flushing of the bag may be difficult to achieve without removal of the bag from the body side member, and the increased risk of spillage caused by removal. Odor is a problem with most of the known bags because of the inability to completely cleanse the bag in place as well as the inability to effectively vent and filter accumulated flatus.

SUMMARY OF THE INVENTION

Embodiments of the disclosed ostomy bag comprise an outer chamber and an inner chamber. The outer chamber comprises an upper portion and a lower portion, wherein the upper portion is defined as the section adjacent to the inner chamber and the lower portion is defined as the section extending below the bottom edge of the inner chamber. The upper portion further comprises an entrance from the stoma to the ostomy bag, and the lower portion is where the excreted bodily wastes are stored for eventual disposal. The fit between the outside surface of the inner chamber and the inside surface of the outer chamber is preferably sized for tight clearance to prevent waste from the lower portion from invading the space between the upper portion and the inner chamber. An interference fit is further provided by the "bellowing" out of the bottom of the inner chamber caused by the biasing member described below.

The inner chamber may comprise a one-way valve that allows entry of wastes into the lower portion of the outer chamber but limits the back flow of the bodily wastes from re-entering the inner chamber. The one-way valve may comprise a biasing member attached to opposing sides of the bottom of one of the walls of the inner chamber. The biasing member may have a length L1 that is greater than the inner chamber bottom wall length L2. The bottom of the inner chamber is urged shut by the force exerted by the biasing member on the bottom of the inner chamber wall.

The disclosed ostomy bag also provides an improved means for cleaning the bag, thereby increasing comfort and convenience to the wearer. The bag may comprise an irrigation system that links to an external fluid source and provides for the flushing of both the inner chamber and the outer chamber simultaneously. The irrigation system may comprise an irrigation connector adapter affixed to the outer chamber and an attachment adapter attached to the inner chamber. The attachment adapter is attached to the irrigation connector adapter, and the irrigation tube. The irrigation tube, which is closed ended, may be routed through a first slit and a second slit that extend through the inner chamber. The irrigation tube comprises slits along the portion of the irrigation tube disposed within the inner chamber and through a large part of the outer chamber. The flushing or rinsing liquid may be introduced into the irrigation tube from a water supply means such as a squeezable reservoir.

The ostomy bag may comprise a vent placed at the upper portion of the outer chamber, and the vent may be used to vent flatus and associated odors that collect within the bag during normal digestion. The vent provides for a slow release of flatus that would otherwise collect in the ostomy bag and cause uncomfortable pressure to the wearer, or exude from the bag when emitted. The vent may further comprise a charcoal filter to strip the noxious smells from the vented flatus. In addition, the vent may comprise scent storage means, such as a tissue sponge, etc., to which scents may be added.

DETAILED DESCRIPTION OF THE INVENTION

Figure 1:
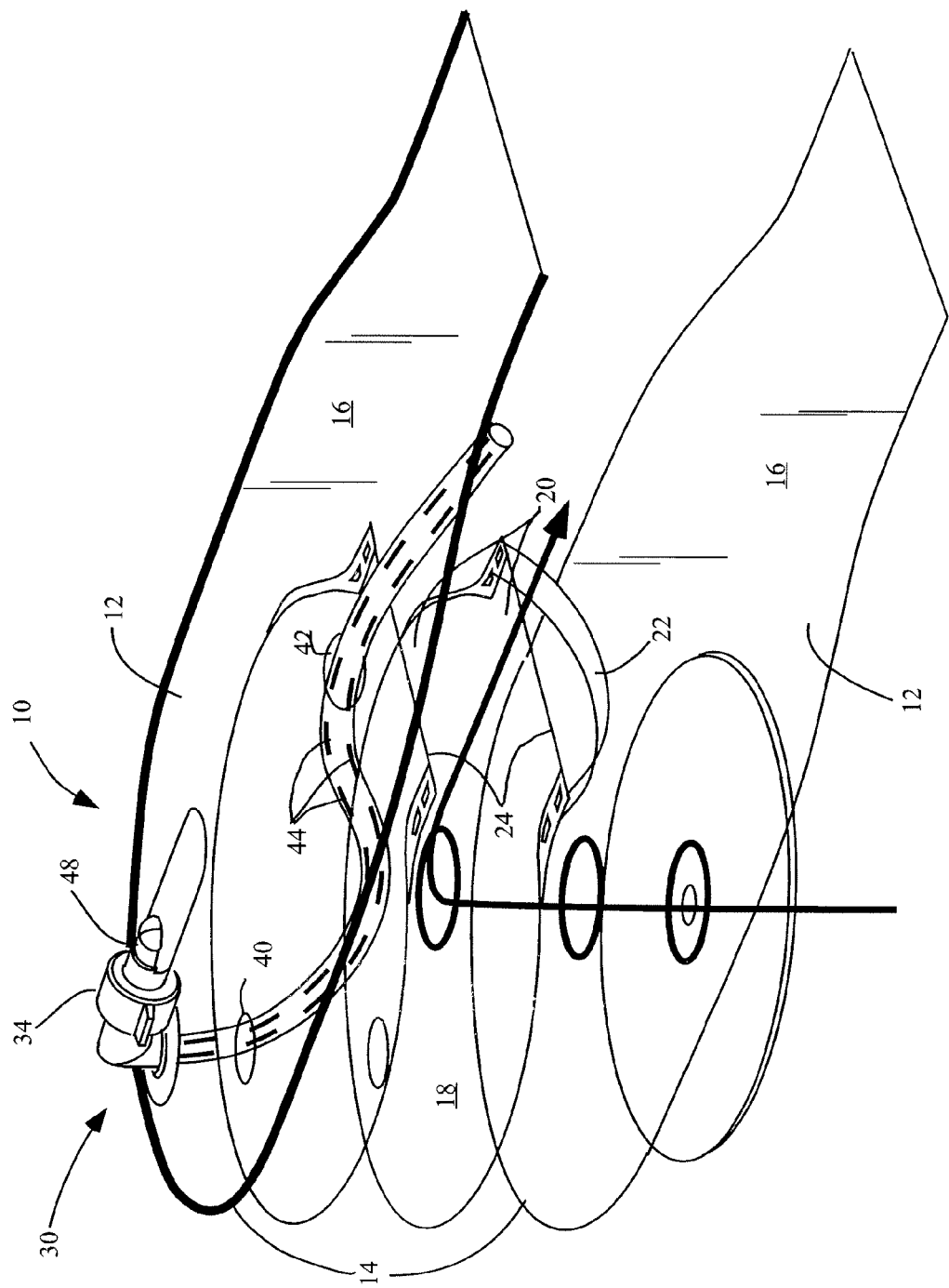
FIG. 1 shows an exploded view of an embodiment of the presently disclosed ostomy bag with cleaning system.
Figure 2:
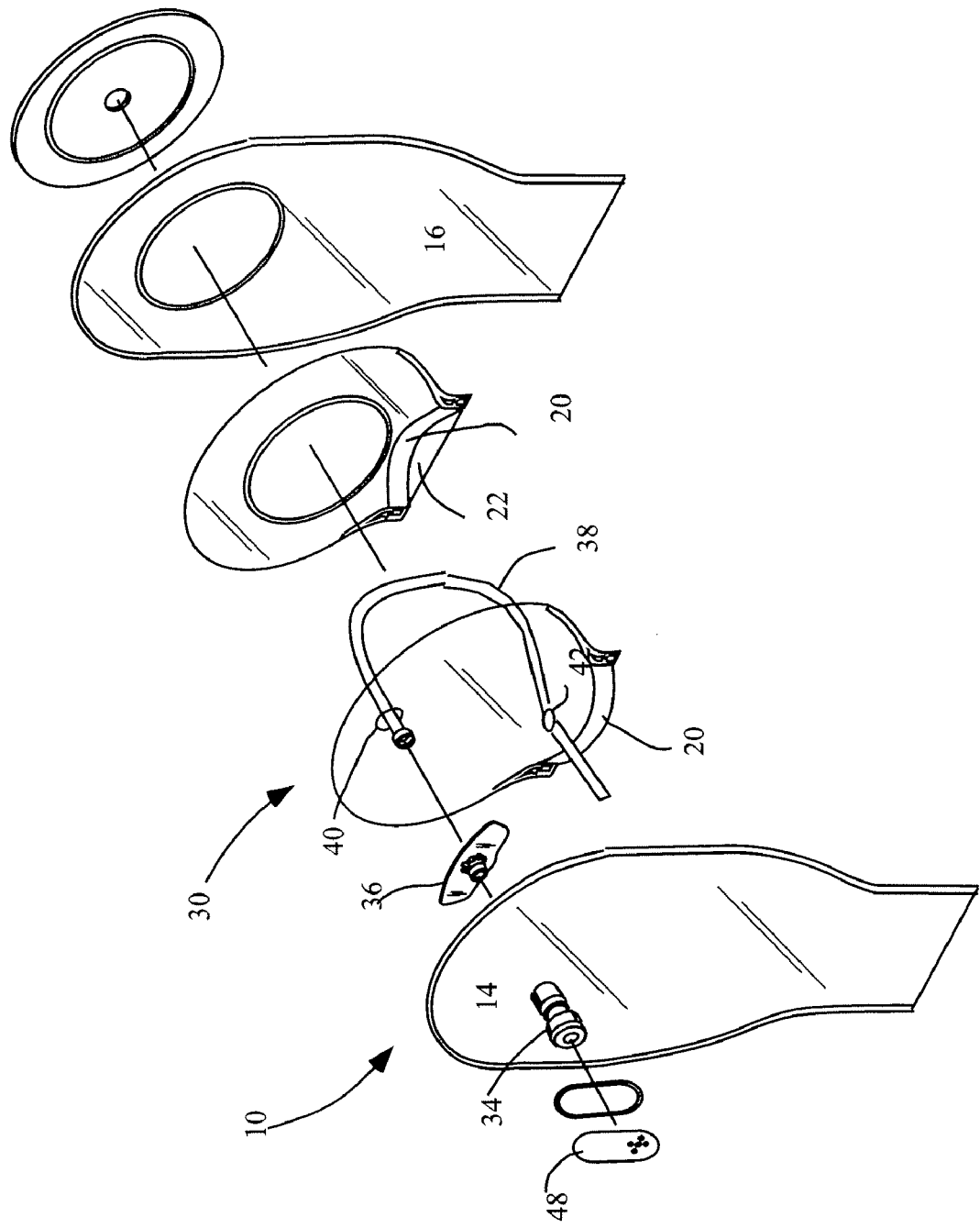
FIG. 2 shows an exploded view of an alternate embodiment of the ostomy bag with cleaning system.
Figure 3:
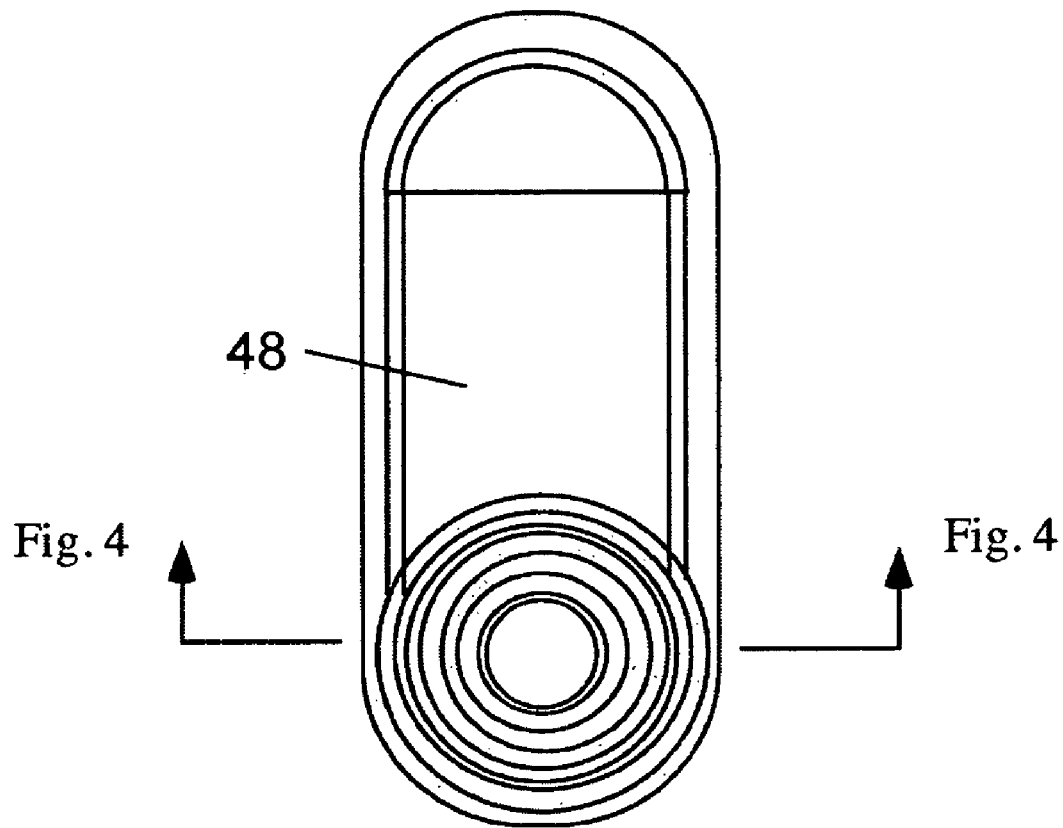
FIG. 3 shows a top view of an embodiment of the filter system.
Figure 6:
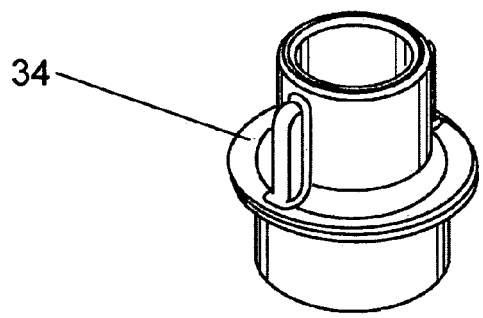
FIG. 6 shows a perspective view of an embodiment of the irrigation hose attachment means.
Figure 7:
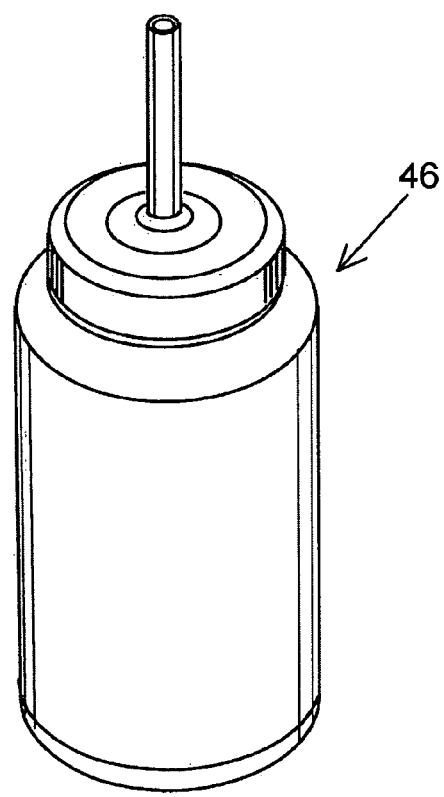
FIG. 7 shows a perspective view of an embodiment of the liquid flushing container of the ostomy bag

Referring now to the Figures, FIGS. 1 through 6 show various views of an embodiment of the disclosed ostomy bag with cleaning system. FIG. 7 shows an embodiment of a squeezable container that may contain fluids utilized for cleaning, sanitizing and deodorizing the ostomy bag. The ostomy bag 10 comprises an outer chamber 12 and an inner chamber 18, wherein the inner chamber 18 is disposed within the outer chamber 12. The outer chamber further comprises an upper portion 14 defined as the section adjacent to the inner chamber 18, and a lower portion 16 defined as the section extending below the bottom edge of the inner chamber 18. The upper portion 14 comprises an entrance for wastes from the stoma to enter the ostomy bag 10, and the lower portion 16 is where the excreted bodily wastes are stored for eventual disposal. The flow of waste into the ostomy bag 10 is generally depicted in FIG. 1 by the directional arrow.

The inner chamber 18 may comprise a one-way valve 20 that allows entry of wastes into the lower portion 16 of the outer chamber 12 but limits the back flow of the bodily wastes from the lower portion 16 of the ostomy bag 10 back into the inner chamber 18. The one-way valve 20 allows free passage of wastes into the lower portion 16 for storage. The one-way valve 20 may comprise a biasing means, such as biasing member 22 attached to opposite sides of one of the walls of the inner chamber 18. The biasing member 22 may have a length that is longer then the length of the bottom 24 of the inner chamber 18 walls. As the biasing member's 22 length L1 is greater than the inner chamber bottom side 24 length L2, the bottom 24 of the inner chamber 18 is urged shut by the force exerted by the biasing member 22 on the bottom 24 of the inner chamber 18. This urging action enhances the one-way valve 20 such that bodily wastes are readily admitted through the valve 20 from the inner chamber 18 to the lower portion 16 for storage, but the reverse is not true. Waste does not flow from the lower portion 16 back into the inner chamber 18. In addition, waste does not readily flow from the lower portion 16 to the upper portion 14, as the biasing member 22 creates an additional barrier against upwards flow from the storage area to the inlet area.

The ostomy bag 10 may comprise an irrigation system 30 that links to an external water source and provides for the flushing of the outer chamber upper 14, the lower portion 16, and the inner chamber 18. The irrigation system 30 comprises an irrigation connector adapter 34 affixed to the outer chamber 12, and an attachment adapter 36 attached to the inner chamber 18. The attachment adapter 36 has a front side that may attach to the irrigation connector adapter 34, and the attachment adapter 36 may itself be attached to an irrigation tube 38 at a back side of the attachment adapter 36. Alternatively the irrigation tube 38 may connect to the irrigation connector adapter 34, and pass through the attachment adapter 36. The irrigation tube 38 is closed-ended, and may be routed through a first slit 40 and a second slit 42 that extend throughout the inner chamber 18 and the outer chamber 12. The irrigation tube 38 may comprise slits 44 along the portion of the irrigation tube 38 that resides within the inner chamber 18 and the lower portion 16 of the outer chamber 12. The slits 44 along the irrigation tube 38 cause the water introduced into the ostomy bag 10 during flushing to disperse from the irrigation tube 38 at a higher pressure. The water may be introduced into the irrigation tube 38 from a squeezable reservoir 46 of the type shown in FIG. 7, or an alternate embodiment may be used to provide liquids for flushing the ostomy bag 10, such as an adapter which allows connecting a water fixture to irrigation tube 38. Use of the reservoir 46 would allow the addition of disinfectants or deodorizers to the flushing water to assist in the cleansing of the ostomy bag 10.

Figure 4:
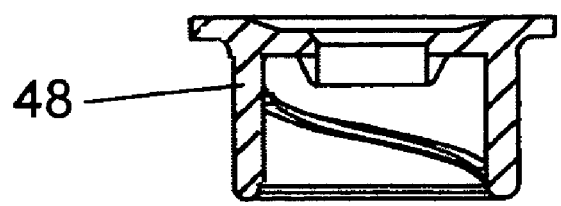
FIG. 4 shows a cross-sectional view of the embodiment of the filter system of FIG. 3, taken essentially along the lines 4-4 of FIG. 3.
Figure 5:
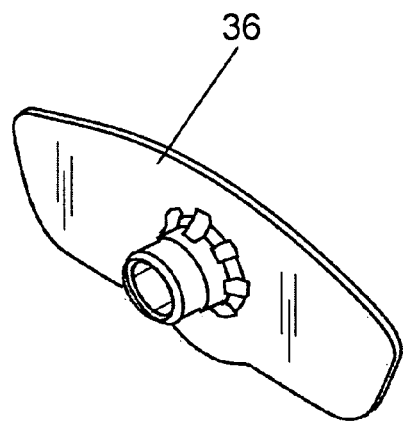
FIG. 5 shows a perspective view of an embodiment of the attachment adapter.

The ostomy bag 10 may comprise a vent 48 placed at the upper portion 14 of the outer chamber 12, and the vent 48 may be used to vent flatus that collects within the bag during normal digestion. The vent 48 may mate through the use of mating parts, embodiments of which are shown in FIG. 4 and FIG. 6. The vent 48 may be attached and removed from the ostomy appliance through the use of a quick disconnect type of attachment, which attaches or releases with a rotation of approximately 180 degrees. Additionally, the vent may comprise the attachment area for introduction of the fluid from the squeezable reservoir 46. The vent 48 may further comprise a charcoal filter to strip the noxious smells from the vented flatus. The vent 48 may also comprise a sponge-like material to which scents may be added, or the vent 48 may comprise a charcoal filter and sponge-like material to which scents may be added.

While the above is a description of various embodiments of the present invention, further modifications may be employed without departing from the spirit and scope of the present invention. Thus the scope of the invention should not be limited by the specific structures disclosed. Instead the true scope of the invention should be determined by the appended claims.

What is claimed is:

1. An ostomy bag comprising:
   an outer chamber comprising a top side and a bottom side;
   an inner chamber disposed within said outer chamber, said inner chamber having a top side and a bottom side, wherein an upper portion of said outer chamber is defined by the presence of said inner chamber and a lower portion of said outer chamber is defined by the absence of said inner chamber;
   a one-way valve at the bottom side of said inner chamber; and
   an irrigation tube having a closed end, said irrigation tube adapted to engage an attachment adapter back side, wherein a portion of said irrigation tube comprises slits.

2. The ostomy bag of claim 1 further comprising an irrigation connector adapter affixed to said outer chamber and an attachment adapter affixed to said inner chamber, said attachment adapter comprising a front side and the back side, said attachment adapter front side adapted to engage said irrigation connector adapter.

3. The ostomy bag of claim 1 wherein said inner chamber further comprises a first slit and a second slit extending through said inner chamber, said irrigation tube threaded through said first slit and said second slit, wherein the introduction of fluid into said ostomy bag through said irrigation tube irrigates both said outer chamber and said inner chamber.

4. The ostomy bag of claim 1 wherein said one-way valve further comprises a flexible biasing member.

5. The ostomy bag of claim 4 wherein said flexible biasing member has a length L1 and said inner chamber bottom side has a length L2, wherein L1 is greater than L2.

6. The ostomy bag of claim 1 further comprising a vent affixed to said outer chamber top side.

7. The ostomy bag of claim 6 wherein said vent further comprises a charcoal filter.

8. The ostomy bag of claim 6 wherein said vent further comprises a medium for deposition of scented materials.

9. An ostomy bag comprising:
   an outer chamber comprising a top side and a bottom side;
   an inner chamber disposed within said outer chamber, said inner chamber having a top side and a bottom side, wherein an upper portion of said outer chamber is defined by the presence of said inner chamber and a lower portion of said outer chamber is defined by the absence of said inner chamber;

an irrigation connector adapter affixed to said outer chamber;

an attachment adapter affixed to said inner chamber, said attachment adapter comprising a front side and a back side, said attachment adapter front side adapted to engage said irrigation connector adapter;

a first slit and a second slit extending through said inner chamber;

an irrigation tube, said irrigation tube adapted to engage said attachment adapter back side, said irrigation tube threaded through said first slit and said second slit, wherein the introduction of fluid into said ostomy bag through said irrigation tube irrigates both said outer chamber and said inner chamber, wherein said irrigation tube further comprises slits along a portion of said tube.

10. The ostomy bag of claim 9 further comprising a one-way valve at said inner chamber bottom side, said one-way valve further comprising a flexible biasing member affixed to said bottom side, wherein said flexible biasing member has a length $L1$ and said inner chamber bottom side has a length $L2$, wherein $L1$ is greater than $L2$.

11. The ostomy bag of claim 9 further comprising a vent affixed to said outer chamber top side wherein said vent comprises a charcoal filter.

12. An ostomy bag comprising:
an outer chamber comprising a top side and a bottom side;
an inner chamber disposed within said outer chamber, said inner chamber having a top side and a bottom side, wherein an upper portion of said outer chamber is defined by the presence of said inner chamber and a lower portion of said outer chamber is defined by the absence of said inner chamber;

a vent affixed to said outer chamber top side; and an irrigation tube having a closed end, said irrigation tube adapted to engage an attachment adapter back side, wherein a portion of said irrigation tube comprises slits.

13. The ostomy bag of claim 12 further comprising an irrigation connector adapter affixed to said outer chamber and an attachment adapter affixed to said inner chamber, said attachment adapter comprising a front side and the back side, said attachment adapter front side adapted to engage said irrigation connector adapter.

14. The ostomy bag of claim 12 wherein said inner chamber further comprises a first slit and a second slit extending through said inner chamber, said irrigation tube threaded through said first slit and said second slit, wherein the introduction of fluid into said ostomy bag through said irrigation tube irrigates both said outer chamber and said inner chamber.

15. The ostomy bag of claim 12 further comprising a one-way valve at the bottom side of said inner chamber, said one-way valve further comprising a flexible biasing member affixed to said inner chamber bottom side, wherein said flexible biasing member has a length $L1$ and said inner chamber bottom side has a length $L2$, wherein $L1$ is greater than $L2$.

* * * * *